(12) United States Patent
Mullins et al.

(10) Patent No.: US 11,215,544 B2
(45) Date of Patent: Jan. 4, 2022

(54) SYSTEMS AND METHODS FOR AUTOMATICALLY EVALUATING SLURRY PROPERTIES

(71) Applicant: UNIVERSITY OF SOUTH FLORIDA, Tampa, FL (US)

(72) Inventors: Austin Gray Mullins, Bradenton, FL (US); Miles Patrick Mullins, Bradenton, FL (US); Christopher L. Lewis, Plant City, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 253 days.

(21) Appl. No.: 16/326,840

(22) PCT Filed: Aug. 25, 2017

(86) PCT No.: PCT/US2017/048739
§ 371 (c)(1),
(2) Date: Feb. 20, 2019

(87) PCT Pub. No.: WO2018/039636
PCT Pub. Date: Mar. 1, 2018

(65) Prior Publication Data
US 2019/0212239 A1   Jul. 11, 2019

Related U.S. Application Data

(60) Provisional application No. 62/379,320, filed on Aug. 25, 2016.

(51) Int. Cl.
*G01N 11/08* (2006.01)
*G01N 33/38* (2006.01)
(Continued)

(52) U.S. Cl.
CPC .............. *G01N 11/08* (2013.01); *E21B 21/08* (2013.01); *E21B 33/13* (2013.01); *E21B 47/005* (2020.05);
(Continued)

(58) Field of Classification Search
CPC ......... E21B 47/04; E21B 47/06; G01N 11/02; G01N 11/08; G01N 15/06
See application file for complete search history.

(56) References Cited

U.S. PATENT DOCUMENTS 4,120,166 A    10/1978  Brooks
5,006,845 A *   4/1991  Calcar .................. E21B 47/001
                                                    367/81
(Continued)

FOREIGN PATENT DOCUMENTS

CN   200610015367 A     2/2007
CN   201010552452       5/2011
WO   WO-9504869 A1 *    2/1995   ............... G01N 9/26

OTHER PUBLICATIONS

International Search Report based on PCT/US2017/048739, dated Nov. 2, 2017.
(Continued)

*Primary Examiner* — John Fitzgerald

(57) ABSTRACT

In some embodiments, a system for automatically evaluating slurry properties includes a down-hole measurement device configured to be lowered into slurry provided in an excavated hole, the measurement device comprising an outer housing, a flow pump, a flow meter, and a differential pressure sensor, wherein the flow pump is configured to pump slurry through the flow meter, the flow meter is configured to measure a flow rate of the pumped slurry, and the differential pressure sensor is configured to measure a
(Continued)

difference in pressure between the pumped slurry and the slurry outside of the measurement device.

16 Claims, 8 Drawing Sheets

(51) Int. Cl.

| | | |
|---|---|---|
| *E21B 21/08* | (2006.01) | |
| *G01N 11/02* | (2006.01) | |
| *E21B 33/13* | (2006.01) | |
| *E21B 47/005* | (2012.01) | |
| *E21B 47/04* | (2012.01) | |
| *E21B 47/06* | (2012.01) | |
| *E21B 47/10* | (2012.01) | |
| *G01N 15/06* | (2006.01) | |
| *F04B 15/02* | (2006.01) | |
| *F04B 17/03* | (2006.01) | |
| *G01N 15/00* | (2006.01) | |

(52) U.S. Cl.
CPC .............. *E21B 47/04* (2013.01); *E21B 47/06* (2013.01); *E21B 47/10* (2013.01); *G01N 11/02* (2013.01); *G01N 15/06* (2013.01); *G01N 33/383* (2013.01); *F04B 15/02* (2013.01); *F04B 17/03* (2013.01); *G01N 2015/0053* (2013.01)

(56) References Cited

U.S. PATENT DOCUMENTS

| | | | | |
|---|---|---|---|---|
| 5,325,709 | A | | 7/1994 | Lee |
| 5,622,223 | A | * | 4/1997 | Vasquez .................. E21B 49/10 166/100 |
| 5,829,520 | A | | 11/1998 | Johnson |
| 6,097,310 | A | | 8/2000 | Harrell |
| 7,036,362 | B2 | * | 5/2006 | Haddad .................. G01N 11/08 73/152.05 |
| 7,320,366 | B2 | * | 1/2008 | Steele .................... E21B 43/017 166/117.5 |
| 7,784,330 | B2 | * | 8/2010 | Angelescu ............. G01N 11/08 73/54.09 |
| 8,004,324 | B2 | | 8/2011 | Tajima |
| 2004/0139798 | A1 | * | 7/2004 | Haddad .................. G01N 11/08 73/152.42 |
| 2006/0180316 | A1 | * | 8/2006 | Steele .................... E21B 43/017 166/381 |
| 2008/0228424 | A1 | * | 9/2008 | Grosser .................. G01N 11/08 702/100 |
| 2009/0090172 | A1 | * | 4/2009 | Angelescu ............. G01N 11/08 73/54.14 |
| 2011/0276187 | A1 | | 11/2011 | Ciglenec |
| 2013/0025359 | A1 | * | 1/2013 | Cartellieri ............. E21B 49/081 73/152.55 |
| 2013/0081460 | A1 | * | 4/2013 | Xiao ....................... E21B 47/10 73/152.29 |
| 2014/0000864 | A1 | * | 1/2014 | Fielder, III ............ E21B 43/128 166/65.1 |
| 2015/0053414 | A1 | * | 2/2015 | Reid ...................... F04D 29/406 166/372 |
| 2015/0176389 | A1 | | 6/2015 | Hsu et al. |
| 2016/0010451 | A1 | * | 1/2016 | Melo ..................... E21B 43/128 702/12 |
| 2016/0341581 | A1 | * | 11/2016 | Singfield ................... G01F 1/74 |
| 2016/0348500 | A1 | * | 12/2016 | Piscsalko .................. E02D 1/02 |
| 2017/0030172 | A1 | * | 2/2017 | Fielder, III ............ E21B 43/128 |
| 2017/0058664 | A1 | * | 3/2017 | Xiao ....................... E21B 47/10 |
| 2017/0138189 | A1 | * | 5/2017 | Ahmad ..................... G01F 1/34 |
| 2018/0328162 | A1 | * | 11/2018 | Hjulstad ............... E21B 47/005 |
| 2019/0234209 | A1 | * | 8/2019 | Ejim ......................... G01N 9/36 |
| 2019/0330971 | A1 | * | 10/2019 | Xiao ......................... G01F 1/74 |

OTHER PUBLICATIONS

Mullins, Automated Device to Measure Slurry Properti3es in Drilled Shafts, USF Scholar Commons, Jul. 1, 2016, pp. 27, 90-152.

Mullins, M. and Mullins, G. (2018). "Automated Down-hole Testing System for Drilled Shaft Slurry," 10th International Conference on Stress Wave Theory and Testing Methods for Deep Foundations Jun. 27-29, 2018 in San Diego, CA (presentation).

Mullins, G. and Mullins, M. (2016). Field Device to Measure Viscosity, Density, and Other Slurry Properties in Drilled Shafts, FDOT Project No. BDV25-977-08, Final Report, 265 pp.

Mullins, G. and Mullins, M. (2016). "Field Device to Measure Viscosity, Density, and Other Slurry Properties in Drilled Shafts," Geotechnical Research in Progress (GRIP) seminar series, Presented to FDOT State Materials Office, Gainesville, FL. Aug. 9.

Mullins, M. and Mullins, G., (2019). "Automated Down-Hole Testing System for Drilled Shaft Slurry," 10th International Conference on Stress Wave Theory and Testing Methods for Deep Foundations, ASTM STP1611, P. Bullock, G. Verbeek, S. Paikowsky, and D. Tara, Eds., ASTM International, West Conshohocken, PA, pp. 128-144, http://dx.doi.org/10.1520/STP1611201701463 (archival journal of proceedings).

Mullins, M., Vomacka, J. and Mullins, G. (2017). "Automated Device to Measure Slurry Properties in Shaft Excavations," 7th Annual ASCE Wissa Lecture Series, Poster Presentation.

Mullins, G. and Mullins, M. (2015). "Field Device to Measure Viscosity, Density, and Other Slurry Properties in Drilled Shafts," Geotechnical Research in Progress (GRIP) seminar series, Presented to FDOT State Materials Office, Gainesville, FL. Aug. 19.

Mullins, M., Vomacka, J. and Mullins, G. (2016). "Automated Device to Measure Slurry Properties in Shaft Excavations," 6th Annual ASCE Wissa Lecture Series, Poster Presentation.

\* cited by examiner

SYSTEMS AND METHODS FOR AUTOMATICALLY EVALUATING SLURRY PROPERTIES

CROSS-REFERENCE TO RELATED APPLICATIONS

This application is the 35 U.S.C. § 371 national stage application of PCT Application No. PCT/US2017/048739, filed Aug. 25, 2017, where the PCT claims the benefit of and priority to U.S. Provisional Application Ser. No. 62/379,320, filed Aug. 25, 2016, both of which are herein incorporated by reference in their entireties.

BACKGROUND

Slurry is the fluid within a drilled shaft excavation that is introduced when an excavation is deeper than the water table or where additional stability is needed for loose, sandy, dry soils. Construction practices vary greatly throughout the country and the world, but slurry levels should be maintained above the existing ground water level by a suitable margin. It should be further noted that at no point is it acceptable to dig below the water table and allow the ground water to fill the excavation as a means to introduce slurry as this loosens the surrounding soil and promotes side wall collapse. While slurries can be categorized as mineral, polymer, or natural, the most widely used slurry type is mineral slurry formed by mixing dry clay powder with water. Depending on the environmental conditions, either bentonite or attapulgite powder may be used (attapulgite being used in saline water conditions).

Although both mineral and polymer slurries have been shown to be effective in stabilizing an excavation, the mechanisms by which they provide this stability are quite different. Mineral slurries (often made from bentonite powder and water) depend on a minimum density (or viscosity) to ensure a significant clay mineral concentration has been achieved and to provide a sufficient lateral pressure on the excavation walls. Stability is further enhanced by the impervious barrier (filter cake) that quickly forms, confining the slurry within the excavation. Without adequate clay mineral concentration, the filter cake will not form. Therefore, the slurry density and viscosity provide a measure of slurry suitability. The effectiveness of mineral slurries to form a filter cake/layer and sufficient lateral pressure allows the required fluid head to be the least of all slurry types.

Newer clay slurry products are now available that are enhanced with polymer additives that can perform equally well, but at lower clay/polymer powder concentrations. These products, known as high-yield products, are compared on the basis of viscosities and not density. High-yield products produce on the order of 200 barrels (1 bbl=42 gals) of slurry for every 2000 pounds (lbs) of powder whereas pure bentonite powders produce only 90 bbls of slurry for every 2000 lbs of powder (both having similar viscosity). This equates to 0.23 lbs/gal and 0.53 lbs/gal for high yield and pure bentonite products, respectively. As both pure and high-yield products are likely to be used on any given project, viscosity becomes a more important property and density is less telling of the true slurry performance potential. However, because the density is lower when using high-yield products, a higher differential head between slurry level and ground water is needed to provide the same net effective lateral pressure against the side walls.

Slurry properties may require adjustments as different soils are encountered to provide a minimum performance level. As a result, slurry testing is often required to track slurry performance. Numerous tests and types of equipment have been developed for use in the field. Florida Standard Specifications for Road and Bridge Construction, Section 455 (FDOT, 2013) requires viscosity and pH values of the slurry to be determined every 2 hours for the first 8 hours of excavation, and then every 4 hours thereafter on 10 foot intervals starting at the bottom of excavation. The high frequency early on is to provide quick feedback as to the soil conditions and its effect on the slurry health. For example, if organic soil is encountered, the lower pH of the soil will cause the bentonite in the slurry to flocculate and thereby lose viscosity. Likewise, salinity in the soil or ground water can have the same effect. Early detection of these conditions prevents side wall sloughing due to performance deterioration of slurry. The slurry density, Marsh funnel viscosity, pH, and sand content are the most common field tests. Sand content is most important just prior to concreting.

Proper performance of mineral slurries used to stabilize drilled shaft excavations is maintained by assuring the density, viscosity, pH, and sand content stay within prescribed limits. These limits have been set either by past experience, research findings, and/or by manufacturer recommended values. However, field slurry testing is time consuming as all measurements are manually performed. With the overwhelming advances in digital down-hole devices, it is not unreasonable to assume that slurry property tests are equally applicable to this trend.

Each of the slurry tests and equipment outlined above has contributory components that may aid in the development of an automated down-hole slurry testing device. By automating slurry testing, there exists the potential to improve the quality of the field data and the speed with which the information is collected.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

From the above discussion, it can be appreciated that it would be desirable to automate down-hole slurry testing. Disclosed herein are systems and methods for automatically evaluating slurry properties. In some embodiments, the systems and methods are specifically used to determine the viscosity, density, and suspended solids content (e.g., sand content) of the slurry at multiple depths within an excavated hole. By automating these measurements, the slurry properties can be evaluated much faster and with much less effort.

In the following disclosure, various specific embodiments are described. It is to be understood that those embodiments are example implementations of the disclosed inventions and that alternative embodiments are possible. All such embodiments are intended to fall within the scope of this disclosure.

Disclosed herein are systems and methods for automatically evaluating slurry properties. The systems and methods incorporate a down-hole measurement device that can be lowered into the slurry within an excavated hole with a rigid connection or flexible tether in similar manner to lowering a diving bell into a body of water. The measurement device can be used to measure parameters that can be used to determine viscosity, density, and suspended solids content at any depth of the device, which can be tracked with a top-side depth encoder wheel (or other depth measuring device). The systems and methods can further incorporate a top-side computerized data collection system in electrical communication with the measurement device that receives measurement data from the device and computes the slurry properties at the depth of the measurement device. During operation, the system can be used to determine the slurry properties at multiple discrete depths or in a continuous fashion as the measurement device is lowered. Because the system automates the process, slurry evaluation at any particular depth can be performed in a manner of seconds as opposed to a manner of minutes.

Figure 1:
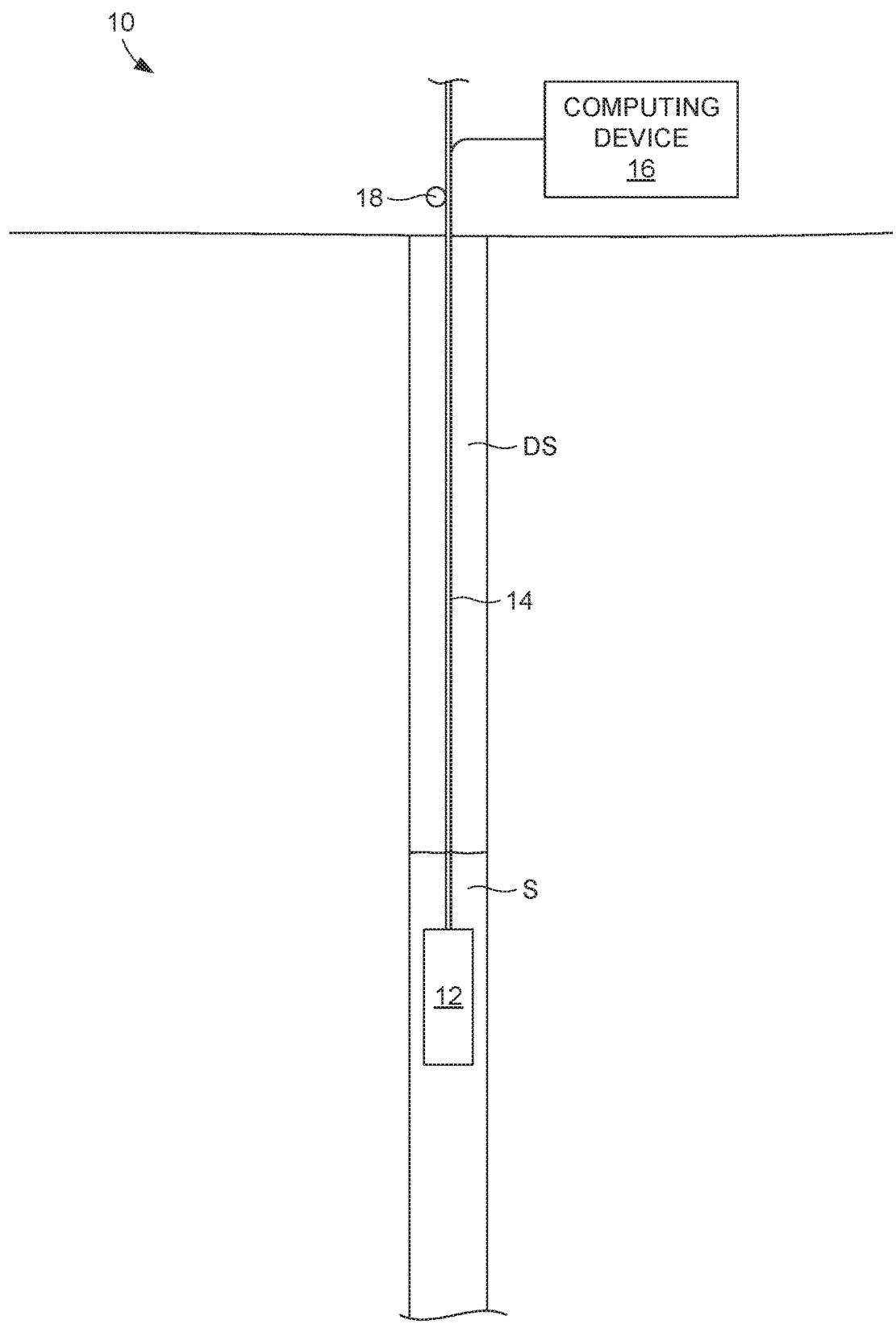
FIG. 1 is a schematic view of an embodiment of a system for automatically evaluating slurry properties.

FIG. 1 illustrates an embodiment of a system 10 for automatically evaluating slurry properties. The system 10 generally includes a down-hole measurement device 12, a tether 14, and a computerized data collection system 16 that is in electrical communication with the measurement device (either at the top of the excavation or incorporated within the down-hole unit). The data collection system 16 can comprise a computer (e.g., laptop computer) that executes software (i.e., computer instructions and/or logic stored on a non-transitory computer-readable medium) that can calculate viscosity, density, and suspended solids content from data collected by the measurement device 12. In the figure, the measurement device 12 has been lowered into slurry, S, contained within a drilled shaft, DS, with the tether 14. An appropriate lowering mechanism (not shown), manual or mechanized, can be used to achieve such lowering. As is further shown in the figure, the depth to which the measurement device 12 is lowered into the drilled shaft can be monitored with a depth measurement device 18, such as an encoder wheel.

Figure 2:
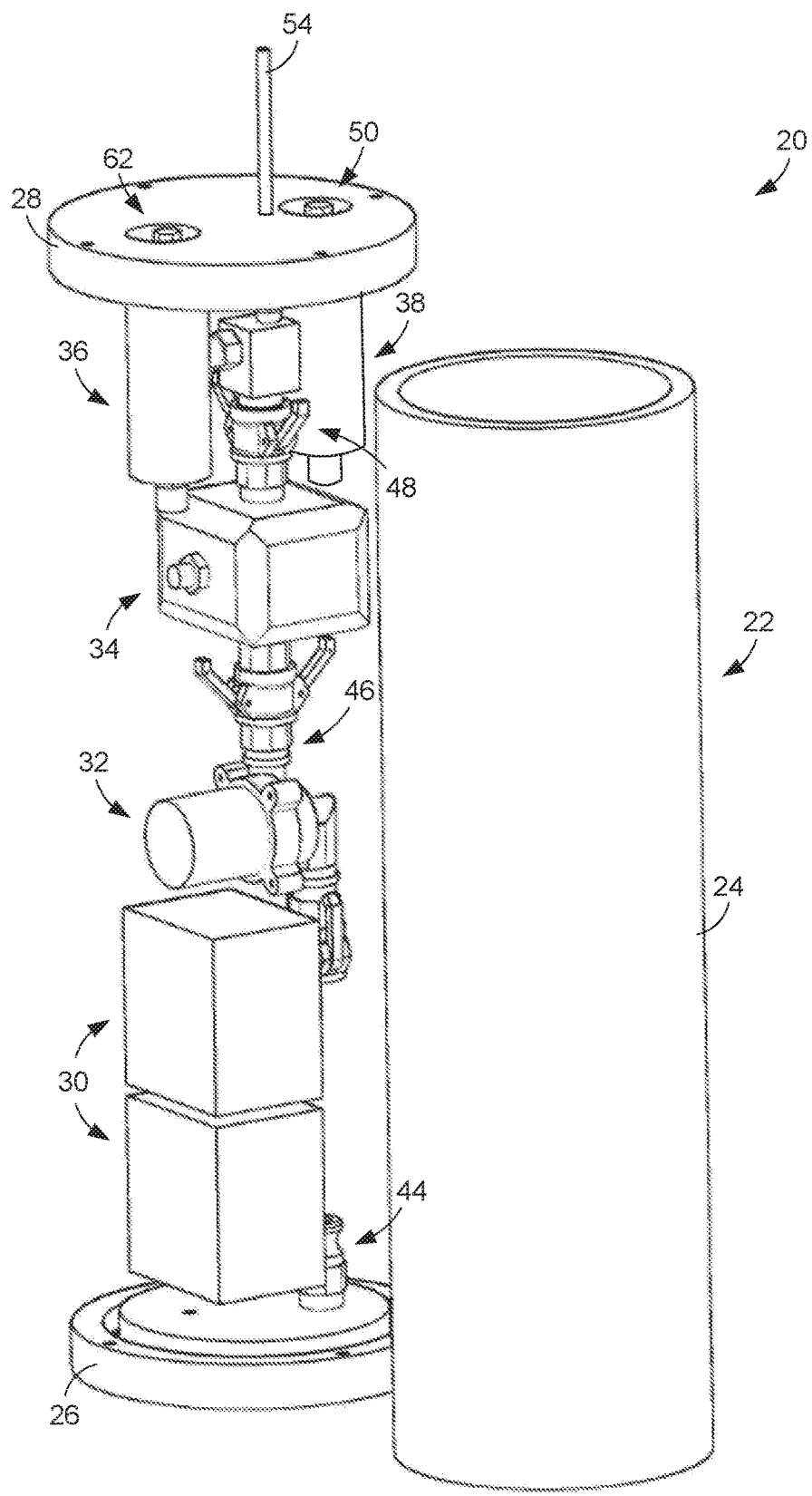
FIG. 2 is an exploded perspective view of a first embodiment of a down-hole measurement device that can be lowered into slurry within an excavated hole for the purpose of determining slurry properties.

FIG. 2 illustrates a first embodiment for a down-hole measurement device 20 that can form part of the system 10 shown in FIG. 1. The measurement device 20 comprises an outer housing 22 that is comprised by an elongated, hollow body 24, a bottom end cap 26, and a top end cap 28. Each of these components can be made of a strong, durable material, such as steel, aluminum, or plastic. In the embodiment of in FIG. 2, the body 24 is a cylindrical tube and the end caps 26, 28 are circular. In some embodiments, the measurement device 20 can be approximately 24 to 30 inches long and have a diameter of approximately 6 to 8 inches.

Figure 3:
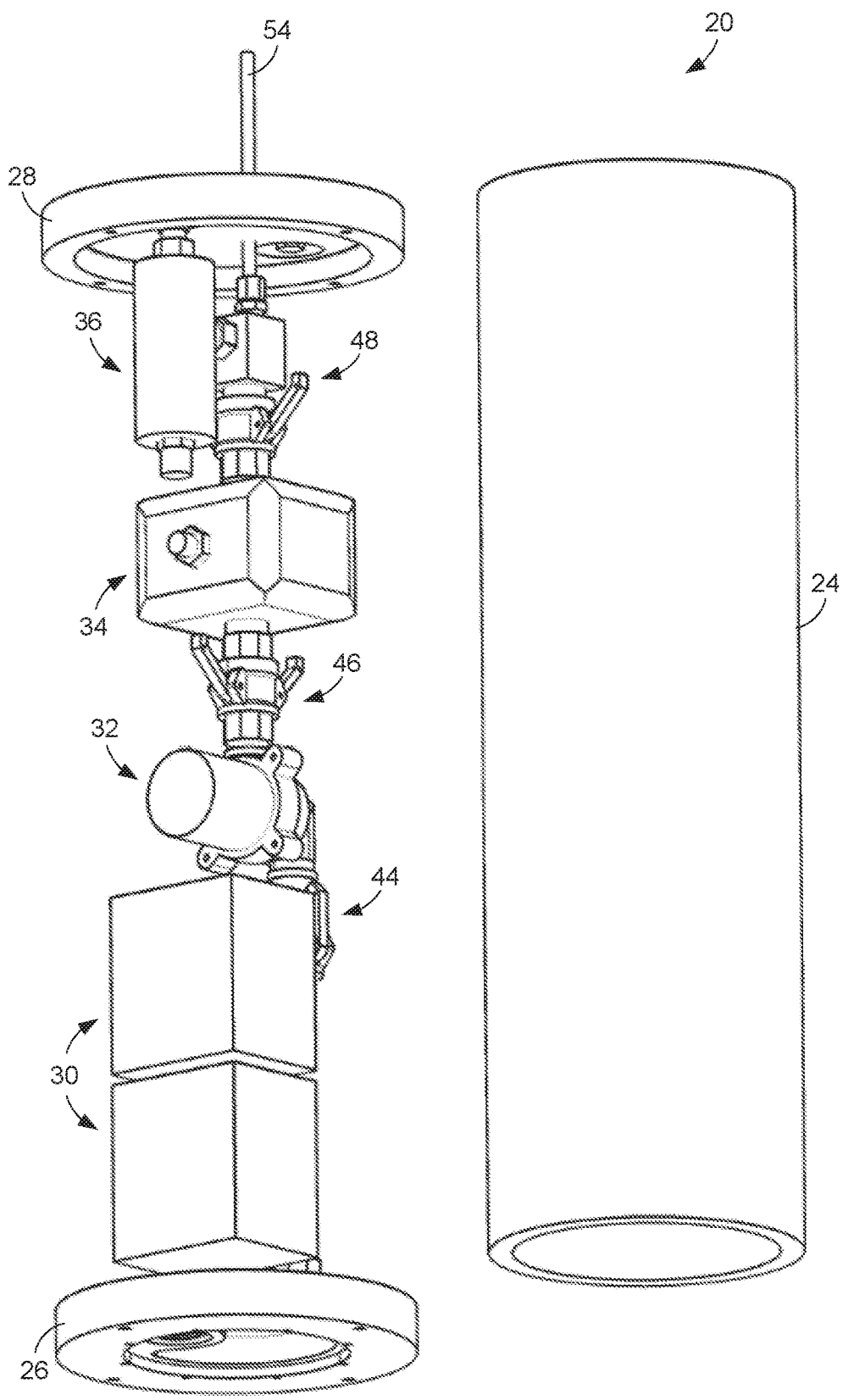
FIG. 3 is a further exploded perspective view of the measurement device of FIG. 2 that identifies the components used to determine slurry viscosity.

FIG. 2 further illustrates various internal components of the measurement device 20 that are contained within the outer housing 22. These components include 5 battery packs 30 that are used to power the electrical components within the measurement device 20, a flow pump 32, a flow meter 34, and first and second differential pressure sensors 36 and 38. FIG. 3 is a further illustration of the measurement device 20, wherein only the components used to determine slurry viscosity are shown. As shown in this figure, these components include the bottom 10 end cap 26, the flow pump 32, the flow meter 34, and the first differential pressure sensor 36.

Figure 4:
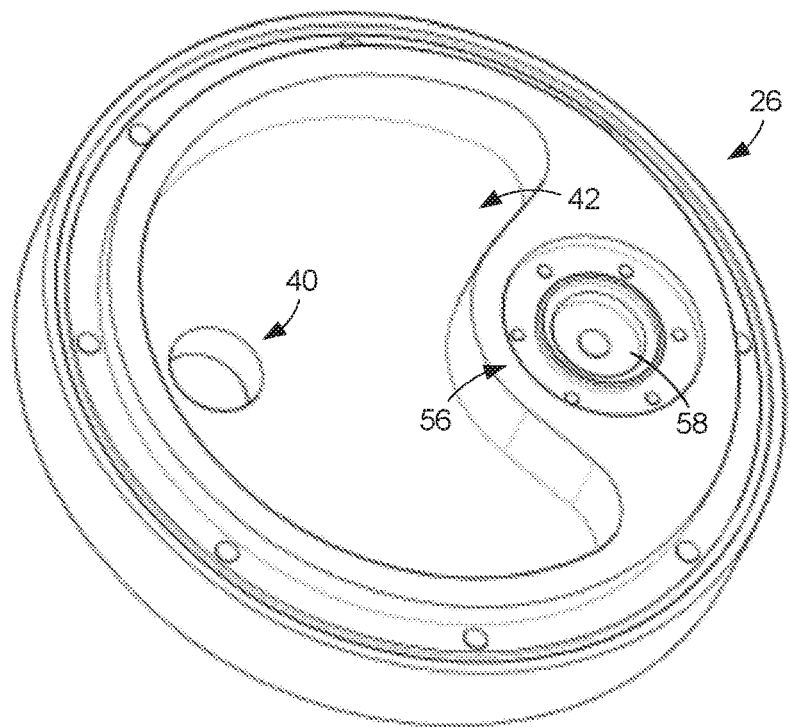
FIG. 4 is a perspective view of a bottom end cap of the measurement device of FIG. 2.

During operation of the measurement device 20, the flow pump 32 draws in slurry in which the measurement device is immersed from the bottom of the device. In particular, slurry is drawn up through a port 40 provided in a pick-up chamber 42 formed in the bottom of the bottom end cap 26, as shown in FIG. 4. This slurry passes through the port 40 and into a conduit 44 (see FIGS. 2, 3, and 4), such as a pipe, and is drawn into the flow pump 32. The pick-up chamber 42 can be covered with a screen (not shown) that filters out large particles within the slurry that could clog the measurement device 20. In some embodiments, the screen is a number 10 sieve. In some embodiments, the flow pump 22 can comprise a direct current (DC) adjustable flow pump, such as the Model DC50C pump from ZKSF.

With reference back to FIG. 3, the flow pump 32 pumps the slurry through a further conduit 46 (e.g., pipe) to the flow meter 34, which measures the rate of flow of the pumped slurry. In some embodiments, the flow meter 34 comprises a magnetic flux flow meter. While Doppler type meters are well suited to fluids with suspended solids, magnetic flux flow meters were found to be the most robust flow meter as they comprise no internal moving parts that would be vulnerable to wear and provided the best resolution and accuracy.

Figure 5:
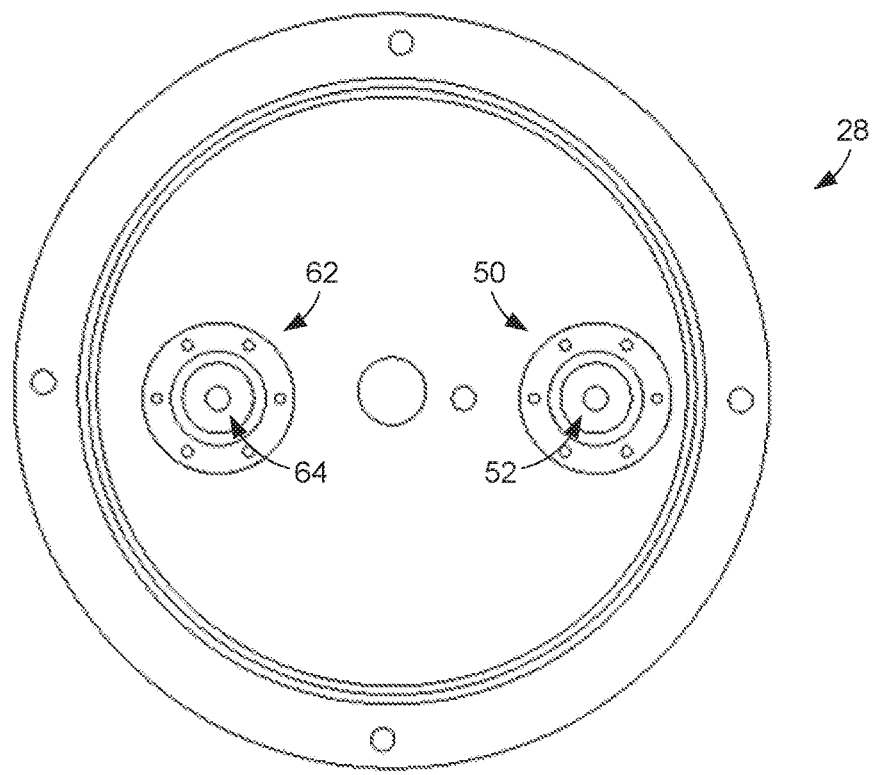
FIG. 5 is a plan view of a top end cap of the device of FIG. 2.

After passing through the flow meter 34, the slurry is delivered through a further conduit (e.g., pipe) 48 so as to flow past the first differential pressure sensor 36. The first differential pressure sensor 36 measures a first pressure signal from the pumped slurry as well as a second pressure signal from the slurry that surrounds the measurement device 20. As such, the first differential pressure sensor 36 can measure the difference in pressure between the slurry pumped through the measurement device and the slurry that surrounds the measurement device. The first pressure signal is obtained from a first sensor element contained within the first differential pressure sensor 36 that is in fluid communication with the slurry flowing past the pressure sensor. The second pressure signal is obtained from a first pressure transmitter 50 provided on the top of the top end cap 28, as shown in FIG. 5. This transmitter 50 includes a flexible (e.g., rubber) membrane (not shown) that separates the exterior slurry from a transmitter fluid (e.g., oil) that is contained in a cavity 52 positioned below the membrane. The pressure exerted by the exterior slurry is transmitted through the membrane to the transmitter fluid so that the pressure can be measured by a second sensor element contained within the first differential pressure sensor 36.

In some embodiments, the first differential pressure sensor 36 comprises a differential pressure transducer. The advantage of a differential transducer is two-fold. First, as all slurry P vs Q curves are based on the pressure across a nozzle, the differential transducer simultaneously tracks the increasing outflow pressure as the slurry depth increases. Second, the transducer range is only required to withstand the pressure caused by the flow pump 32 and not the high pressure that accompanies great excavation depths (a 200 ft excavation≈90 psi; pressure across nozzle≈1 to 2 psi). In this way, the resolution of the transducer can be fully focused on a small pressure range without worries of damaging the pressure sensitive membrane. In some embodiments, the first differential pressure sensor 36 can comprise the Omegadyne Model PX81D0-010D5T differential pressure transducer. This transducer has a 10 pounds per square inch (psi) maximum pressure range, but even smaller ranges are available.

After the pumped slurry passes by the first differential pressure sensor 36, it is discharged from the measurement device 20 through a discharge nozzle 54. As shown in FIGS. 2 and 3, the discharge nozzle 54 can have a vertical orientation, in which case slurry can be discharged from the top end of the measurement device 20. An advantage of a top-exit discharge nozzle 54 is that it facilitates assembly and service. In some embodiments, the discharge nozzle 54 can be approximately 6 inches long and have an inner diameter of approximately 3/16 inches.

As described above, there are various conduits that connect the interior components of the measurement device 20. It is noted that, in some embodiments, the conduits can connect to their associated components with cam-lock quick-connect fittings to aid in both assembly and service.

The components identified in FIG. 3 are used to measure the parameters that can be used to compute viscosity. In particular, the viscosity of the slurry can be computed by the top-side computerized data collection system 16 (FIG. 1) with knowledge of the flow rate, measured by the flow meter 34, and the differential pressure, measured by the first differential pressure sensor 36. The measurement device 20 is lowered into the slurry and, once it reaches a desired depth, further decent is halted. Baseline measurements can then be taken which essentially tares out any effects caused by increased slurry density and the height difference between the discharge nozzle 54 and the reference transmitter locations.

Once the baseline measurements have been taken, the flow pump 32 can be activated to drive slurry through the measurement device 20 in the manner described above. The flow pump 32 can be operated for a few seconds and the flow rate and pressure measurements can be taken. These parameters can then be transmitted via a communication cable (not shown) to the computerized data collection system for determination of the viscosity. In particular, the computing system calculates the viscosity based upon equations that relate the flow rate, pressure, and viscosity of slurry. For example, the viscosity can be calculated using Equation 1 (which uses specific dimensions for the discharge nozzle 54):

$$\text{Viscosity} = \text{EXP}\left(\text{Pressure} - \frac{-1.5Flow^2 - 12.4Flow^{-2}}{1.84Flow^2 + 4Flow + 0.6}\right) \quad \text{Equation 1}$$

Figure 6:
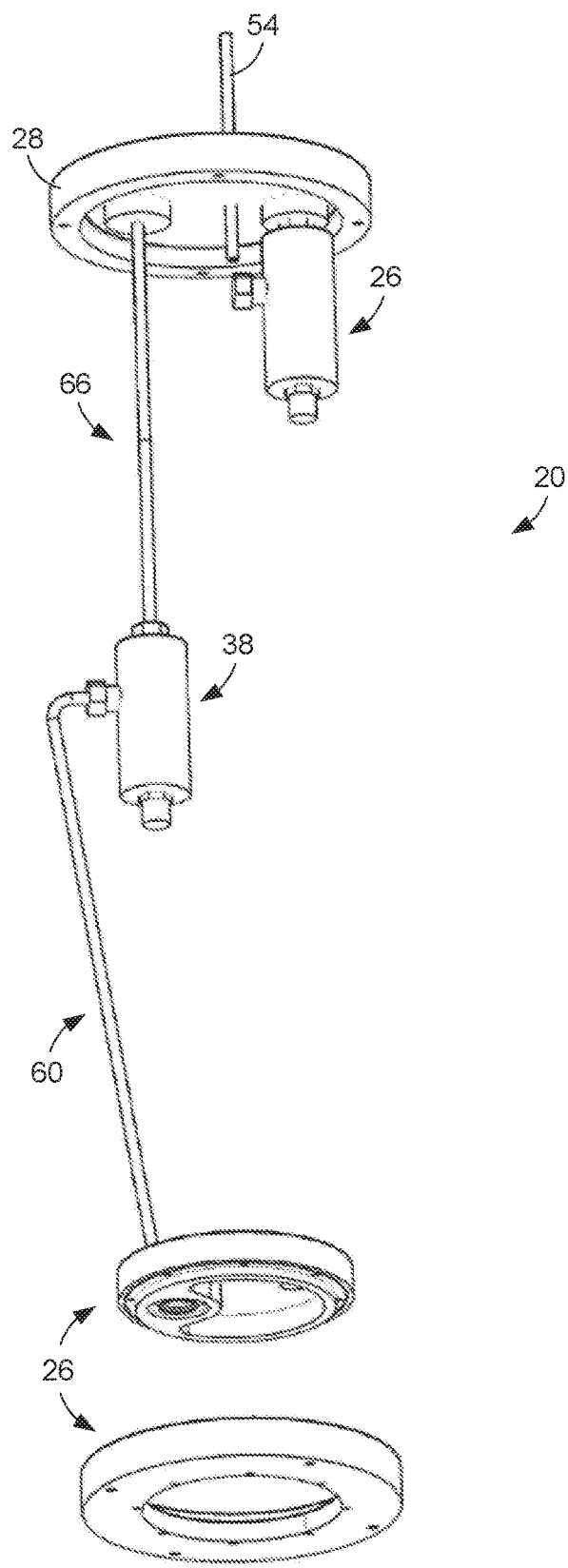
FIG. 6 is a further exploded perspective view of the measurement device of FIG. 2 that identifies the components used to determine slurry density.

FIG. 6 is a further illustration of the measurement device 20, wherein the components used to determine slurry density are shown. As depicted in this figure, these components include the second differential pressure sensor 38, which measures the pressure of the exterior slurry at the bottom and at the top of the measurement device 20. As with the first differential pressure sensor 36, the second differential pressure sensor 38 can be a differential pressure transducer. As shown in FIG. 6, the second differential pressure sensor 38 is connected to a pressure transmitter 56 provided in the bottom of the bottom end cap 26, as shown in FIG. 4. This transmitter 56 also includes a flexible (e.g., rubber) membrane (not shown) that separates the exterior slurry from a transmitter fluid (e.g., oil) that is contained in a cavity 58 positioned below the membrane. The pressure exerted by the exterior slurry is transmitted through the membrane to the transmitter fluid and through a conduit (e.g., tube) 60 so that the pressure can be measured by a first sensor element contained within the second differential pressure sensor 38.

The second differential pressure sensor 38 is also connected to a second pressure transmitter 62 provided in the top of the top end cap 26, as shown in FIG. 5. This transmitter 62 also includes a flexible (e.g., rubber) membrane (not shown) that separates the exterior slurry from a transmitter fluid (e.g., oil) that is contained in a cavity 64 positioned below the membrane. The pressure exerted by the exterior slurry is transmitted through the membrane to the transmitter fluid and through a conduit (e.g., tube) 66 so that the pressure can be measured by a second sensor element contained within the second differential pressure sensor 38.

Once the differential pressure, i.e., the difference between the pressure of the slurry at the bottom of the measurement device 20 and the pressure of the slurry at the top of the device, has been measured, the measurement can be transmitted via the communication cable to the top-side computerized data collection system 16 for determination of the density. In particular, the computerized data collection system 16 calculates the density by dividing the differential pressure by the differential depth. For example, the density can be calculated using Equation 2 (again using specific dimensions for the discharge nozzle 54):

$$\text{Density} = (\text{Pressure}_{bottom} - \text{Pressure}_{top})/\text{Height}_{difference} \quad \text{Equation 2}$$

In addition to the viscosity and density, the suspended solids content can be determined using the data collected by the measurement device 20. In particular, the suspended solids content can be determined from the computed viscosity and the measured density. Using a correlation between viscosity and the amount of slurry products required to achieve a given viscosity, the density component from slurry products can be subtracted from the total density to determine the suspended solids (sand or silt) content that is not actively contributing to gel strength or viscosity. The volumetric suspended solids content (SSC) requires an assumed loose particle packing efficiency or void ratio, as in Equation 3. The SSC is the same as sand content when there is no silt, but otherwise provides a silt inclusive equivalent.

$$SSC = \frac{(\gamma_{meas} - \gamma_{clean})}{(\gamma_w S_g e - \gamma_{mean})} \times 100\% \quad \text{Equation 3}$$

where $\gamma_{meas}$ is the measured density of the soil laden slurry, $S_g$ is the specific gravity of sand, 2.65, e is the void ratio of very loose sand in the API sand content vial, 0.8, $\gamma_w$ is the density of water, and $\gamma_{clean}$ is the density of the clean slurry at a given viscosity which can be estimated for pure bentonite slurry, as per Equation 4:

$$\gamma_{clean} = \frac{V-21}{0.015(V-21)+0.004} \quad \text{Equation 4}$$

and V is the computed viscosity in seconds per quart (sec/qt).

Similar equations for $\gamma_{clean}$ can be prepared for high-yield products as well. Note the 200 bbl high-yield material is roughly half the weight of 90 bbl pure bentonite. The weight contribution of polymer slurry can be fully ignored ($\gamma_{clean} = \gamma_{water}$) making all additional weight in polymer slurry the effect of suspended cuttings.

Figure 7:
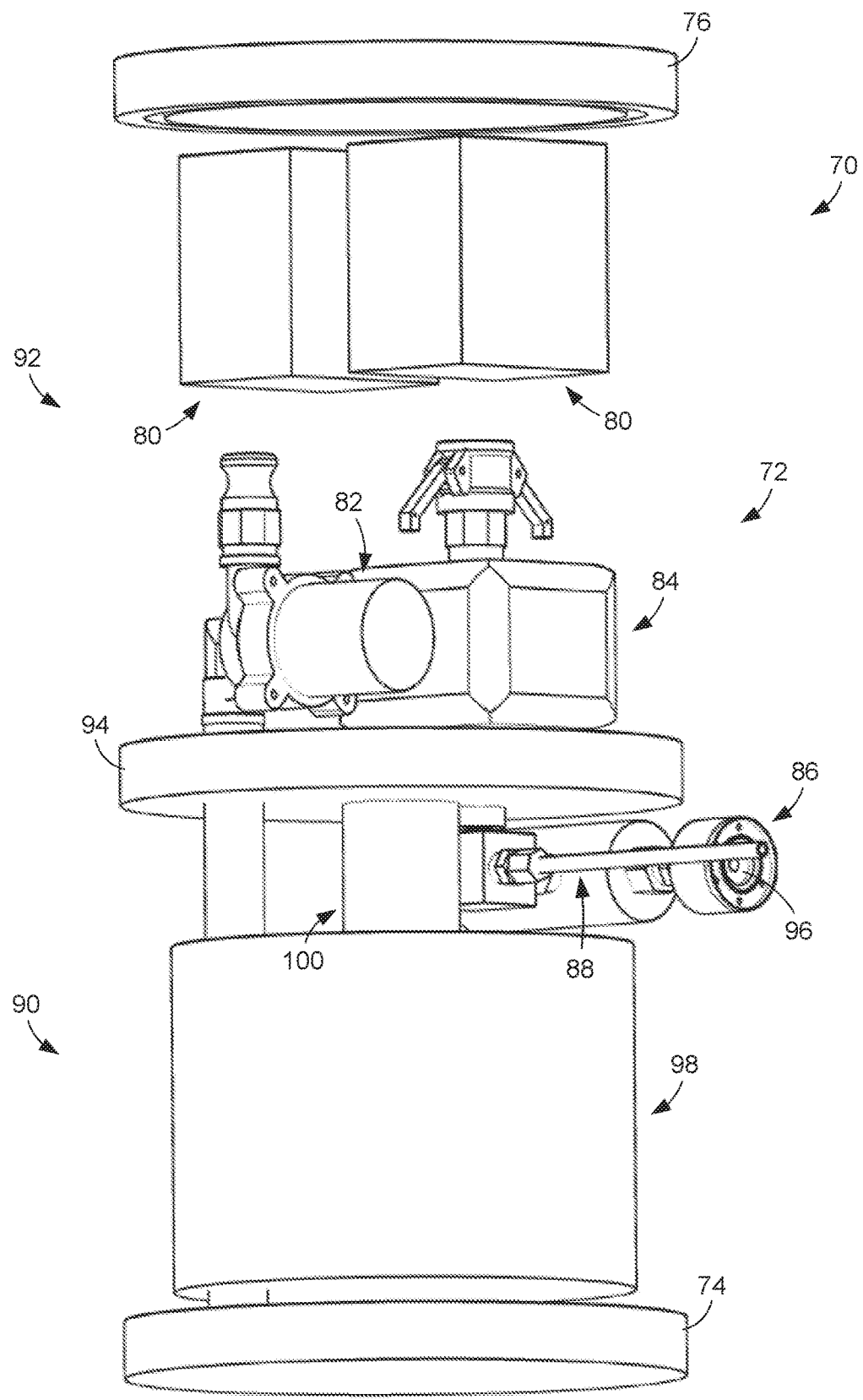
FIG. 7 is an exploded perspective view of a second embodiment of a down-hole measurement device that can be lowered into slurry within an excavated hole for the purpose of determining slurry properties.

FIG. 7 illustrates a second embodiment of a down-hole measurement device 70 that can form part of a system for automatically evaluating slurry properties. The measurement device 70 is similar to the measurement device 20 in several ways. For example, the measurement device 70 comprises an outer housing 72 that includes a bottom end cap 74 and a top end cap 76. The outer housing 72 further includes a hollow body (not shown) that extends between the bottom and top end caps 74, 76. Each of these components can be made of a strong, durable material, such as steel, aluminum, or plastic. In some embodiments, the measurement device 70 can be approximately 10 to 18 inches long and have a diameter of approximately 6 to 8 inches.

The measurement device 70 also includes various components that are housed within the outer housing 72. These components include battery packs 80, a flow pump 82, a flow meter 84, a differential pressure sensor 86, and a discharge nozzle 88. In the embodiment of FIG. 7, however, the measurement device 70 is divided into a lower, wet chamber 90 and an upper, dry chamber 92 by a divider 94 that prevents fluid communication between the two chambers. The flow pump 82 and the flow meter 84 are contained in the dry chamber 92 and are not exposed to slurry, while the differential pressure sensor 86 and the discharge nozzle 88 are immersed in slurry that enters the wet chamber 90 through one or more openings (not shown) formed in the bottom end cap 74.

The measurement device 70 is used to determine viscosity in substantially the same way as the measurement device 20. Accordingly, slurry is driven through the flow meter 84 under the force of the flow pump 82 and the differential pressure is measured by the differential pressure sensor 86, which is in fluid communication with the pressure of the pumped slurry and the exterior slurry via a pressure transmitter 96 provided in the side of the housing 72. Density, however, is determined using a fixed volume 98 of material (e.g., aluminum or plastic) that is suspended by a load cell 100 within the wet chamber 90. When the measurement device 70 is immersed in the slurry, the slurry enters the wet chamber 90 and surrounds the fixed volume 98, which displaces the slurry. The change in weight measured by the load cell 100 can be divided by the volume occupied by the fixed volume 98 to obtain the density of the slurry.

Experiments were performed to evaluate the systems and measurement devices described above. A prototype down-hole measurement device (down-hole unit (DHU)) comprised a clear, water-tight, polyvinyl chloride (PVC) housing with aluminum end caps, a miniature 12-24 VDC pump with a No. 10 filter screen, a low-flow magnetic flux flow meter, a differential pressure transducer, a load cell attached to a 0.1 ft$^3$ cylindrical prism, an on-board rechargeable battery pack, signal conditioners, and an on/off switching relay. All signal leads, charging circuits, and relay trigger wires were connected to the top-side computerized data collection system (CDS) via a 160 foot underwater cable that also served as a lowering/raising tether. While only discrete depths were planned for testing, the prototype system also incorporated an encoder wheel over which the cable was passed to track depth.

The CDS was self-powered with another rechargeable battery pack that was used to power a computer of the CDS, trigger the measurement device power switching relay, and a three-position logic switch that sent data markers to a USB-powered data acquisition unit. The three positions indicated density (switch left) or viscosity (switch right). The center position sent no data markers and was used when descending or initializing the pump.

The testing procedure was as follows: Lower the DHU to the desired depth, switch the logic switch left for density measurements for several seconds (average of several points), switch to center and increase pump flow rate until stable flow and pressure readings are obtained (magnetic flux flow meters are slow to respond), once stable switch logic to right position for viscosity measurements for several seconds, return switch to center position, turn off pump and descend to next depth increment and repeat. One test cycle at a given depth takes approximately 30 seconds. Adding the descent time to the next location, each data point takes between approximately 1 and 2 minutes.

After simple calibration tests of the viscosity and density devices, large scale laboratory and field trials were conducted. Large scale trials involved a 45 foot long, 12 inch inner diameter slurry-filled PVC pipe fastened to the side of the three-story building. The tests were conducted from the roof by alternatively lowering the DHU into clean water and slurry ranging in viscosity from 30 to 50 sec/qt. The benefit of these tests was threefold: simulate field conditions with the benefit of controlling slurry properties, demonstrate the unit could withstand hydrostatic pressure well above simple submersions, and test the data collection systems which now included depth measurements. Field trials were conducted at several shaft construction sites in both polymer and bentonite slurry; three are discussed.

Figure 8:
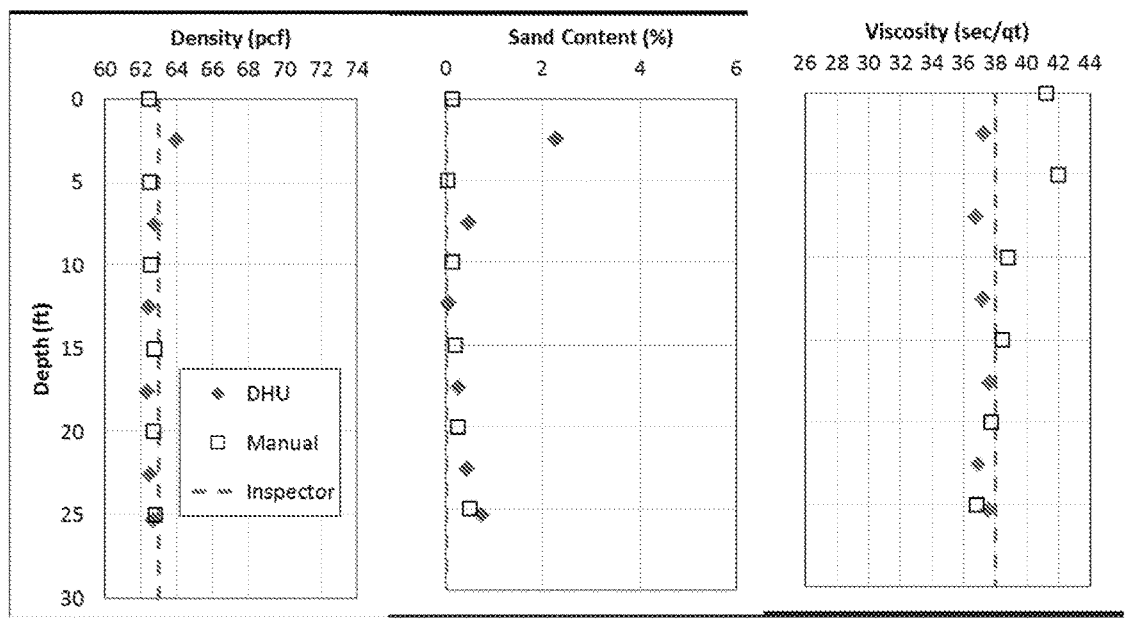
FIG. 8 are graphs that plot slurry testing results from a first test site.

At Site 1, a first DHU similar in design to the measurement device 20 shown in FIG. 2 was used to obtain differential pressure density measurements. The test shaft was 72 inches in diameter, 26 feet long, and was excavated using polymer slurry. The results of one-point tests are shown in FIG. 8 as the dashed line. Manual samples were taken on 5 foot intervals immediately after the automated tests were completed, but were tested the next day in the lab.

The viscosity readings were uniform with depth, which is largely a result of using premixed slurry that was dispensed to the excavation directly from a tanker truck. Inspector values agreed with that recorded by the automated system. Lab testing of the manually recovered samples showed some changes in viscosity with time for some samples which is not uncommon for disturbed polymer slurry that is allowed to sit.

Figure 9:
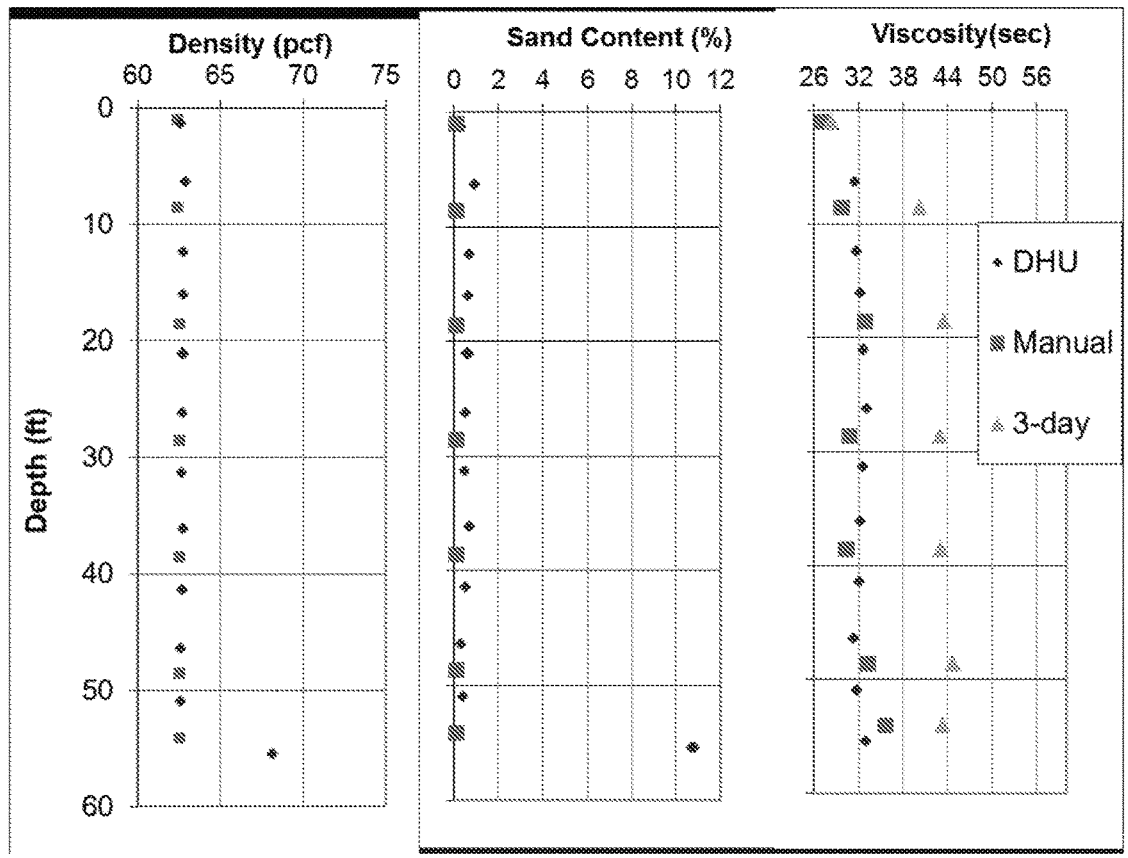
FIG. 9 are graphs that plot slurry testing results from a second test site.

At Site 2, the test shaft was 72 inches in diameter, 60 feet long, and were excavated using polymer slurry. Field and lab testing procedures were performed similar to Site 1, where samples were recovered immediately after automated testing. Automated tests were performed using a second DHU similar in design to the measurement device 70 shown in FIG. 7. Lab testing was performed while the samples were still disturbed and then again 3 days later. FIG. 9 shows good agreement between manual and DHU measurements. Three-day samples showed the effects of polymer chain formation on viscosity when left undisturbed. The solid PVC cylinder of the DHU attached to the bottom of the load cell will register the top of sediment and just before touching shows the highest density, suspended solids and sometimes viscosity. When the DHU touches the bottom, density readings go off scale, thereby defining the exact bottom location.

Figure 10:
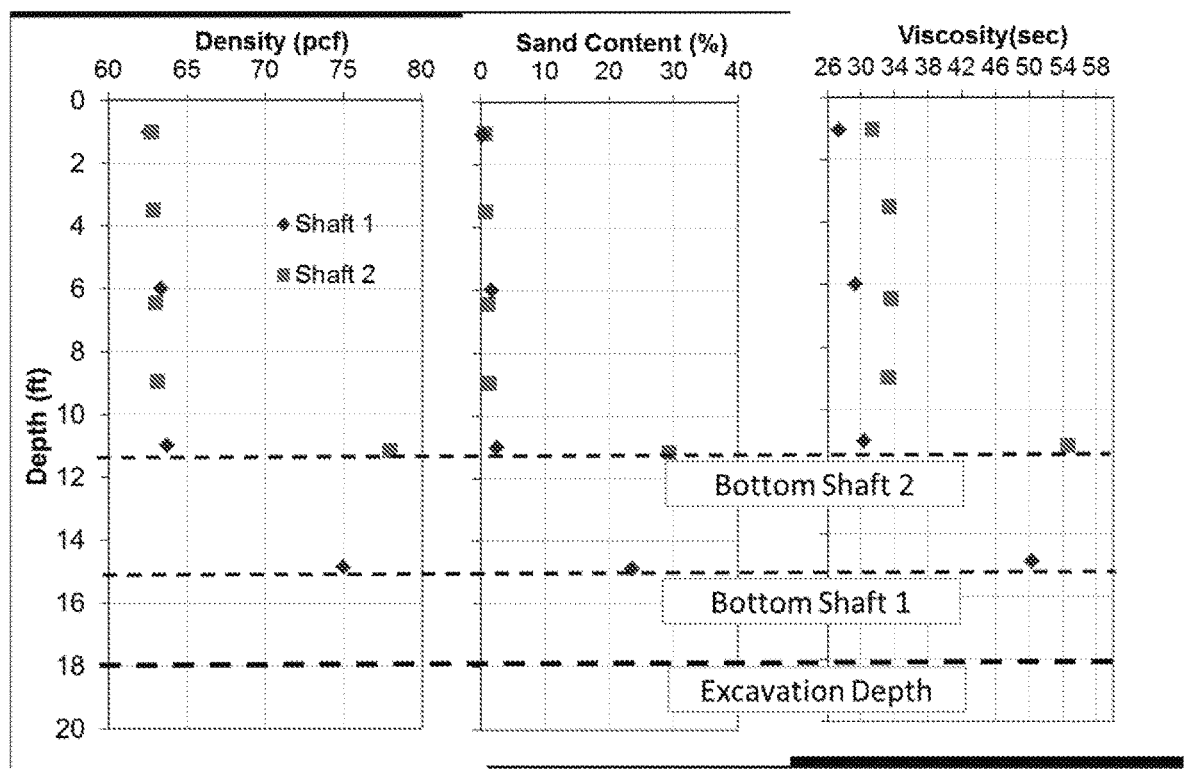
FIG. 10 are graphs that plot slurry testing results from a third test site.

At Site 3, two shafts were tested again using the second DHU. The shafts were 60 inches diameter, 18 feet long (for traffic signals), and were excavated using polymer slurry. Automated testing was performed immediately after reaching the design depth while the reinforcing cage and anchor bolts were being readied. In both cases, the top of sediment was found much shallower than the excavated depth. Shafts 1 and 2 were 3 and 6 feet short, respectively (FIG. 10). In both cases, slurry viscosity was much lower than recommended by the manufacturer (45-55 sec/qt) for fine sandy soils and not much thicker than water (26 sec/qt).

The poor performance of the slurry was due to low viscosity, which, in turn, was a byproduct of the slurry mixing method. Slurry was not premixed. A shallow 4 feet hole was initiated with an auger, a short surface casing was installed, and soil was packed around the perimeter. Using a 2 inch supply line, water was pumped into the casing and dry polymer powder was poured into the open stream. Before excavating below the bottom of casing, the slurry viscosity was approximately 50 sec/qt. Excavation ensued and water was used to refill with occasional scoops of dry powder again poured into the stream. By the time the design depth was reached, only third of the dry polymer pail had been used or about half the manufacturer estimated product needed (CETCO 2017). Slurry was recovered and reused the next day for Shaft 2 with small amounts of extra product added at the onset of slurry preparation in the casing. Note that the Shaft 2 excavation showed slightly higher viscosity values but still exhibited sediment from sloughing.

For both shafts, the excavation was re-drilled before the cage was placed and the inspector was only required to test the bottom of the shaft. The one-point sample recovered and tested passed the recommended viscosity range with values of 47 and 51 sec/qt for Shafts 1 and 2, respectively. Similar values were noted at the bottom of the excavation using the automated system.

For the short shafts tested at Site 3, the ramifications of side-wall sloughing are not as dire as deeper excavations as concreting can be completed more quickly, but it is more than likely that sloughing continued even after the cage was placed. Concrete volumes were estimated to be 10% more than the theoretical volume, but recall, the bottom filled in 16 and 33% of the shaft length for the two shafts. No integrity tests were performed to determine the as-built shaft radius profile; soft toe (or necks) and bulges often have offsetting volume effects.

The proper viscosity slurry that was used to commence drilling (in casing) essentially stayed at the bottom with continued excavation and the thinner water like slurry simply stayed above.

While the 30 foot slurry testing increment did not catch the slurry variation, sampling at smaller intervals with the automated system detected the far-too-thin material which was spot checked and verified by the inspector.

For all three sites, the viscosity was never within the manufacturer's recommended range except perhaps at the bottom. Sites 1 and 3 required slurry testing but only at the bottom using the 30 foot intervals, while Site 2 was not required to test by the owner. The higher viscosity of Site 1 (37-38 sec/qt) did show acceptable performance based on little to no accumulated sediment. Site 2 showed less sediment accumulation relative to Site 3 where 3-day tests (44 sec/qt) indicated that at least the slurry had a higher mix ratio and was mostly uniform. Overnight, the recovered slurry on Site 3 slightly increased in viscosity from 27-30 to 32-33 sec/qt, but still was not enough to maintain stability.

The time of testing with the automated system was surprisingly fast given the experimental nature of the units and data collection software. At Site 1, the actual slurry testing time was 4 minutes for the six depths tested. When including the apparatus setup and break down, the entire testing time was less than 15 minutes. Sites 2 and 3 showed similar time efficiency: 18 minutes for 11 points and 4 minutes for 4 points, respectively. At best, manual readings of viscosity, density, and suspended solids content along with sample recovery take 5 to 10 minutes per depth location.

The invention claimed is:

1. A system for automatically evaluating slurry properties, the system comprising:
   a down-hole measurement device configured to be lowered into slurry provided in an excavated hole, the measurement device comprising an outer housing, a flow pump, a flow meter, and a differential pressure sensor, wherein the flow pump is configured to pump slurry through the flow meter, the flow meter is configured to measure a flow rate of the pumped slurry, and the differential pressure sensor is configured to measure a difference in pressure between the pumped slurry and the slurry outside of the measurement device.

2. The system of claim 1, further comprising a depth measurement device configured to measure a depth to which the measurement device is lowered into the excavated hole.

3. The system of claim 1, wherein the flow pump comprises a direct current (DC) adjustable flow pump.

4. The system of claim 1, wherein the flow meter comprises a magnetic flux flow meter.

5. The system of claim 1, wherein the differential pressure sensor comprises a differential pressure transducer.

6. The system of claim 1, wherein the measurement device further comprises a battery pack.

7. The system of claim 1, wherein the measurement device further comprises a second differential pressure sensor configured to measure a difference in pressure between slurry at the bottom of the measurement device and slurry at the top of the measurement device.

8. The system of claim 7, wherein the differential pressure sensors each measure the pressure of slurry outside of the measurement device using a pressure transmitter that includes a flexible diaphragm that separates the slurry from a transmitter liquid that transmits pressure to a sensor element of the pressure sensor.

9. The system of claim 1, wherein the measurement device comprises a dry chamber in which slurry does not flow and a wet chamber in which slurry flows, wherein the flow pump and flow meter are contained in the dry chamber and the differential pressure sensor is contained in the wet chamber.

10. The system of claim 9, wherein the wet chamber of the measurement device further comprises a fixed volume of material suspended by a load cell and wherein the fixed volume of material is immersed in slurry when the measurement device is immersed in the slurry.

11. A down-hole measurement device configured to be lowered into slurry provided in an excavated hole, the measurement device comprising:
   an outer housing;
   a flow pump contained within the outer housing;
   a flow meter contained within the outer housing; and a differential pressure sensor contained within the outer housing;

wherein the flow pump is configured to pump slurry through the flow meter, the flow meter is configured to measure a flow rate of the pumped slurry, and the differential pressure sensor is configured to measure a difference in pressure between the pumped slurry and the slurry outside of the measurement device.

12. The measurement device of claim 11, further comprising a battery pack contained within the outer housing.

13. The measurement device of claim 11, wherein the measurement device further comprises a second differential pressure sensor configured to measure a difference in pressure between slurry at the bottom of the measurement device and slurry at the top of the measurement device.

14. The measurement device of claim 13, wherein the differential pressure sensors each measure the pressure of slurry outside of the measurement device using a pressure transmitter that includes a flexible diaphragm that separates the slurry from a transmitter liquid that transmits pressure to a sensor element of the pressure sensor.

15. The measurement device of claim 11, wherein the measurement device comprises a dry chamber in which slurry does not flow and a wet chamber in which slurry flows, wherein the flow pump and flow meter are contained in the dry chamber and the differential pressure sensor is contained in the wet chamber.

16. The measurement device of claim 15, wherein the wet chamber of the measurement device further comprises a fixed volume of material suspended by a load cell and wherein the fixed volume of material is immersed in slurry when the measurement device is immersed in the slurry.

* * * * *

UNITED STATES PATENT AND TRADEMARK OFFICE
CERTIFICATE OF CORRECTION

PATENT NO. : 11,215,544 B2
APPLICATION NO. : 16/326840
DATED : January 4, 2022
INVENTOR(S) : Austin Gray Mullins et al.

Page 1 of 1

It is certified that error appears in the above-identified patent and that said Letters Patent is hereby corrected as shown below:

In the Specification

Column 4, Line 10, "include 5 battery" should be --include battery--.

Column 4, Line 17, "bottom 10 end" should be --bottom end--.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*